US008424533B2

(12) United States Patent
Sanchez

(10) Patent No.: US 8,424,533 B2
(45) Date of Patent: Apr. 23, 2013

(54) BOLERO-STYLE STRAIT JACKET

(75) Inventor: Gerardo Sanchez, Los Angeles, CA (US)

(73) Assignee: The Stockroom, Inc., Los Angeles, CA (US)

( * ) Notice: Subject to any disclaimer, the term of this patent is extended or adjusted under 35 U.S.C. 154(b) by 739 days.

(21) Appl. No.: 12/506,747

(22) Filed: Jul. 21, 2009

(65) Prior Publication Data

US 2011/0308535 A1 Dec. 22, 2011

Related U.S. Application Data

(63) Continuation-in-part of application No. 12/006,373, filed on Jan. 2, 2008, now abandoned.

(51) Int. Cl.
| | | |
|---|---|---|
| *A61B 19/00* | (2006.01) | |
| *E05B 73/00* | (2006.01) | |
| *A41D 13/00* | (2006.01) | |
| *A47C 31/00* | (2006.01) | |

(52) U.S. Cl.
USPC ............ 128/869; 70/15; 2/69; 297/465

(58) Field of Classification Search ............ 128/846, 128/869, 870, 873, 874, 876; 2/69, 115, 2/114, 108, 106, 105, 93, 85, 83, 80, 95; 297/464, 465; 70/15–17

See application file for complete search history.

(56) References Cited

U.S. PATENT DOCUMENTS

| 1,047,457 | A | * | 12/1912 | Steimer | 70/16 |
|---|---|---|---|---|---|
| 1,751,872 | A | * | 3/1930 | Medaugh | 2/159 |
| 2,062,586 | A | * | 12/1936 | Lawrence | 128/875 |
| 2,388,234 | A | * | 11/1945 | Abel | 2/51 |
| 4,971,073 | A | * | 11/1990 | Schneider | 128/874 |
| 5,027,833 | A | * | 7/1991 | Calkin | 128/870 |
| 5,031,639 | A | * | 7/1991 | Wolfer | 128/874 |
| 6,024,091 | A | * | 2/2000 | Bennett | 128/873 |

OTHER PUBLICATIONS

Internet Website: http://web.archive.org/web/20010522232730/http://www.fetters-leather.com; May 22, 2001.*

* cited by examiner

*Primary Examiner* — Patricia Bianco
*Assistant Examiner* — Tarla Patel
(74) *Attorney, Agent, or Firm* — Hughes Socol Piers Resnick & Dym, Ltd.; Todd S. Parkhurst

(57) ABSTRACT

A strait jacket is disclosed, which is adapted to fit wearers of more than one clothing size. The strait jacket has a jacket torso body comprising at least two panels, each panel terminating at a lower edge located adjacent to but below the wearer's underarms. Sleeves extend from the torso body to distal ends, and each sleeve has a length greater than the length of the wearer's arms. The distal end of each sleeve includes a fastening device to permit the sleeve to be fastened to the opposite sleeve and to a belt by suitable fasteners at a position behind the wearer's back. An annular jacket collar is located above the jacket torso body, and a strap extends downwardly from the collar. In one embodiment of the invention, the strap extends under the wearer's crotch. A belt strap is adapted to be secured about the wearer's mid rib cage and is further adapted to be attached to the chest strap at a posterior position; and, if desired, at an anterior position.

8 Claims, 3 Drawing Sheets

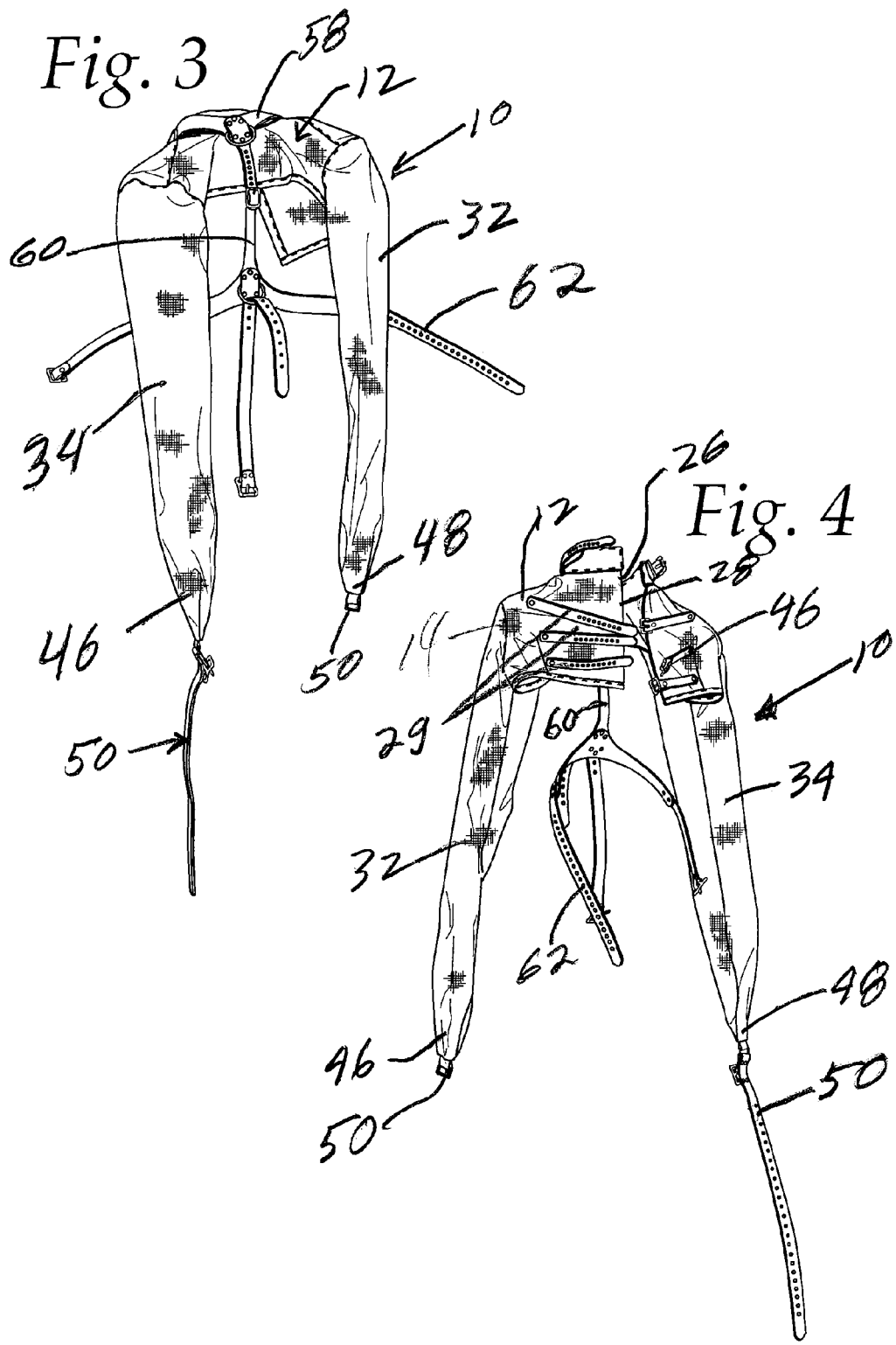

BOLERO-STYLE STRAIT JACKET

This application is a continuation-in-part of U.S. Ser. No. 12/006,373 filed Jan. 2, 2008 entitled "Strait Jacket" which is incorporated herein in its entirety by reference.

BACKGTOUND OF THE INVENTION

Conventional strait jackets are garments intended to restrain a potentially violent mentally or emotionally distressed patient or other individual requiring restraint from use of his or her arms, so as to prevent injury to himself or herself, or to others. Traditional straitjackets have torso bodies which extend down to, or finish, at or near the hip level. Sleeves attached to the torso body each have lengths which extend beyond the wearer's fingertips. Straps or other fasteners are attached to the distal ends of each sleeve. Once the patient's arms are inside the sleeves and the back is fastened, the jacket arms are crossed at the center front of the body and the strap from one sleeve extends around the back of the body, and can be fastened to the other sleeve.

Some known jackets have a crotch strap which extends downwardly from the front of the torso body or a jacket collar, under the patient's crotch, and upwardly to a fastening point on the jacket torso body rear. This crotch strap prohibits the wearer from pulling the jacket over his or her head and thus removing it.

Less conventional employment of strait jackets include use in adult play involving domination and other activities. The strait jacket embodying the invention claimed herein is especially adapted for use in these adult play activities.

It is an object of this invention to provide a strait jacket having a design which permits the jacket to be used with a variety of wearers having a variety of clothing and body sizes and shapes.

It is another object of the invention to provide a strait jacket which permits the use of medical or other devices which require direct skin contact, such as EKG electrodes, ultrasound systems, or adult toys.

It is yet another object of the invention to provide a strait jacket which minimizes chafing and overheating to the wearers, especially struggling patients or players.

Still another object of the invention is to provide a strait jacket the size and shape of which minimizes intimidation of the wearer and other observers.

A further object of the intention is to provide a strait jacket which has a minimal cost to manufacture.

Other objects and advantages of the invention will be apparent upon reading the following detailed description and upon reference to the drawings. Throughout the drawings, like reference numerals refer to like parts.

DESCRIPTION OF THE DRAWINGS

FIG. 3 is a front elevational view of the jacket.

FIG. 4 is a rear elevational view of the jacket.

DETAILED DESCRIPTION

While the invention will be described in connection with a preferred embodiment, it will be understood that it is not intended to limit the invention to this embodiment. On the contrary, it is intended to cover all alternatives, modifications and equivalents as may be included within the spirit and scope of the invention.

Turning to the drawings, there is shown a strait jacket 10 embodying the invention. The strait jacket can be made of any suitable material. In the illustrated embodiment of the present invention, a fabric having the characteristics of canvas is preferred.

Figure 1:
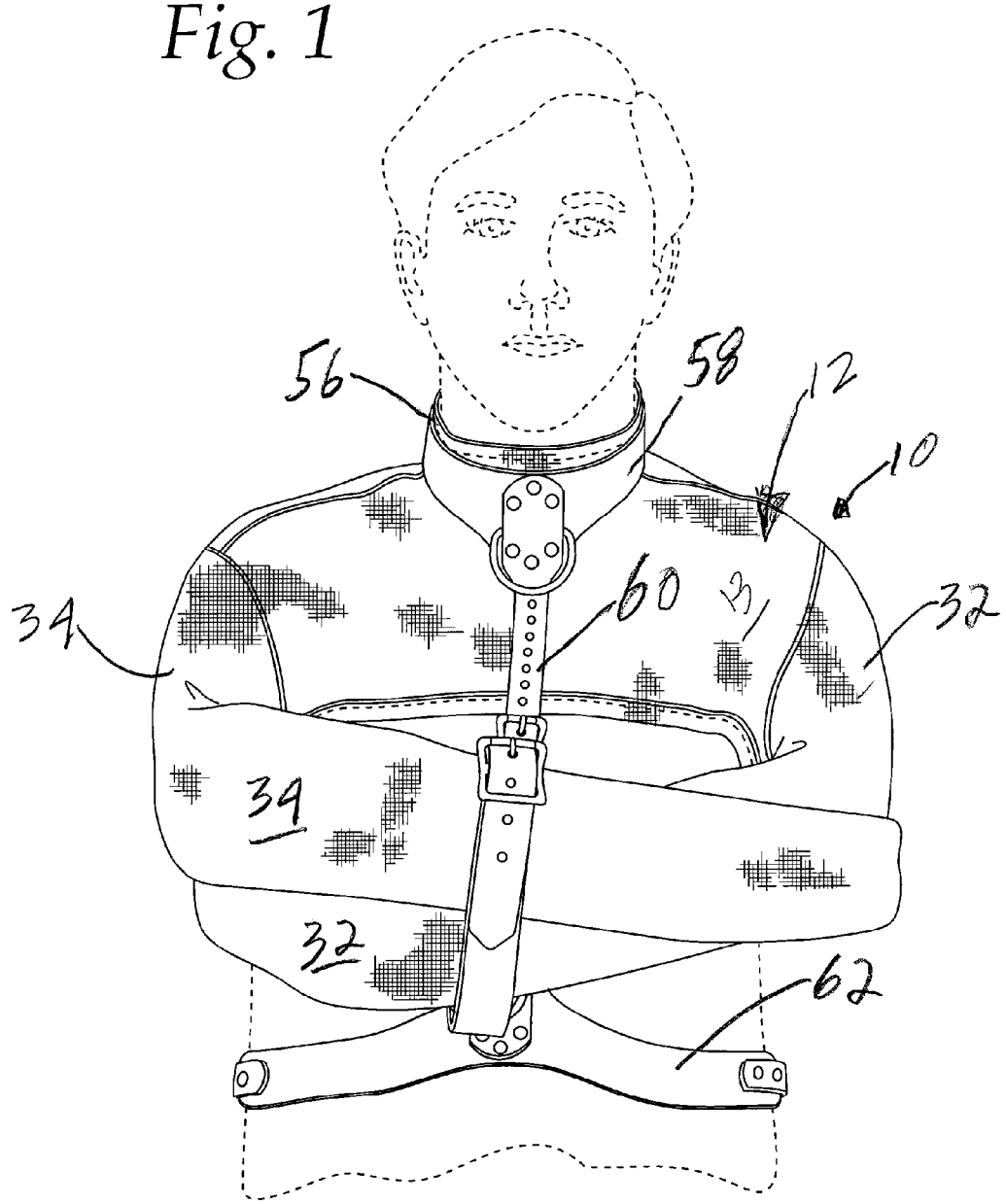
FIG. 1 is a front elevational view of the jacket as it appears when it is being worn.
Figure 2:
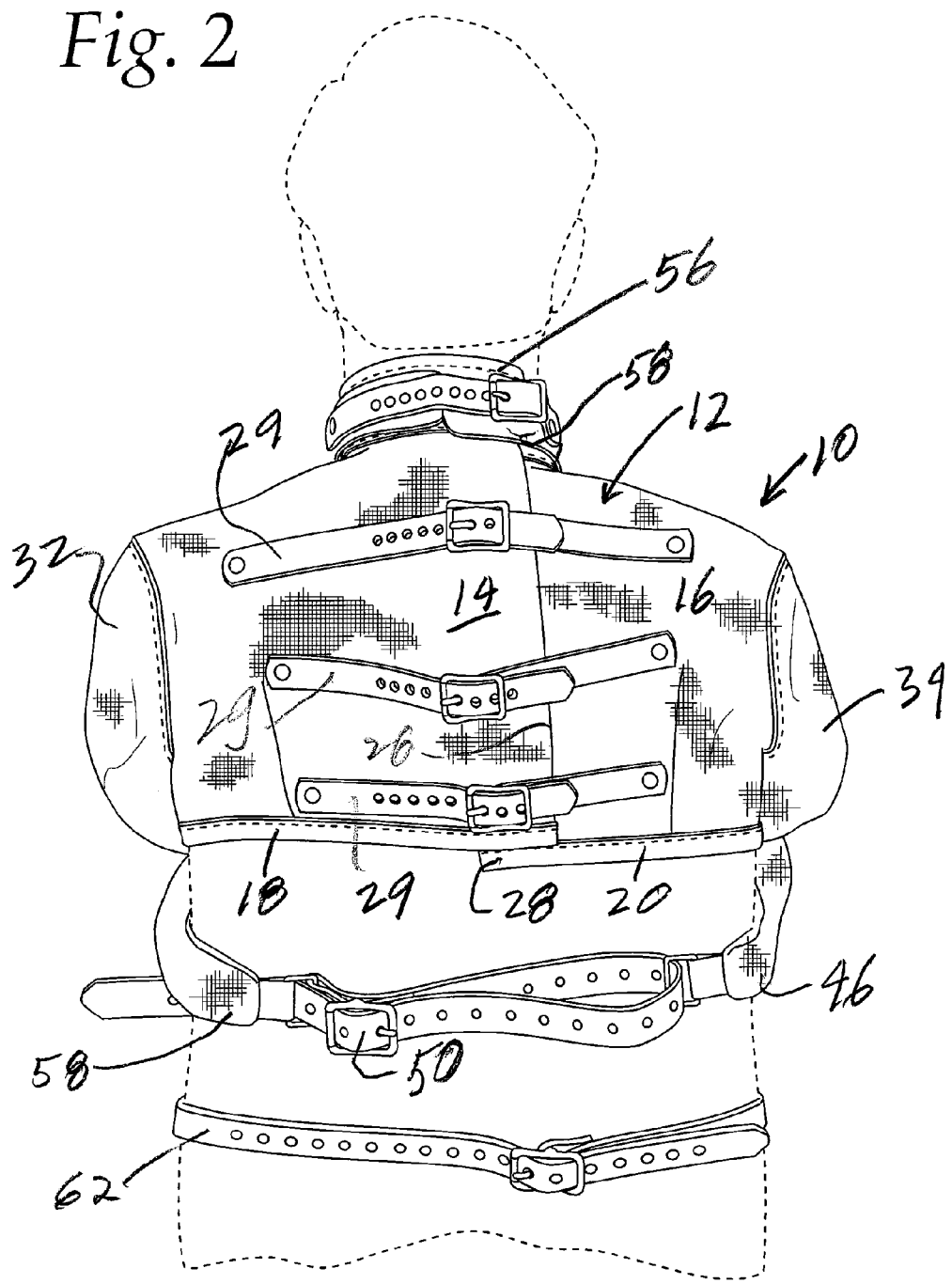
FIG. 2 is a rear elevational view of the jacket as it appears when it is being worn.

To enable the strait jacket 10 to fit a variety of wearers having a variety of clothing sizes and body sizes and shapes in accordance with the invention, the strait jacket has a bolero-style jacket torso body 12 which comprises a closed front 13 and at least two back panels 14, 16. Each back panel 14, 16 terminates at a lower edge 18, 20 adjacent to, but below the wearer's under arms as shown in FIGS. 1 and 2. Here the jacket terminates above the wearer's waist and below the underarms or shoulders.

In a preferred embodiment, these lower edges 18, 20 are located about 2 inches below the wearers under arms, and, more specifically, the edges illustrated here are located 1-⅜" below the wearer's under arms. Thus, the strait jacket fabric covers only the wearer's upper back, upper chest, lower neck and arms. This permits the use of medical devices which require skin contact, such as EKG electrodes, ultrasound systems, and adult toys in accordance with another aspect of the invention. In accordance with another use of the invention, the jacket exposes much of the wearer's torso to the direct activities of an adult player. In addition, the minimal aspect of the strait jacket minimizes chafing and overheating of wearers, especially struggling wearers; and may minimize the intimidation of a wearer and other observers or players.

In accordance with a further aspect of the invention, the two panels 14, 16 each have respective back side edges 26 and 28. When the strait jacket is being worn, these edges 26 and 28 can be spaced apart from one another, or they can be configured so that the panels overlap so as to define a strait jacket partial body which will fit a wide variety of body shapes and sizes, in accordance with one aspect of the invention. One or more strap means 29 extend between the back panels 14, 16. The straps 29 are provided with buckles, or other known devices, for adjusting the effective length of the straps 29 so as to snugly secure the strait jacket bolero-style body around the wearer.

Extending from the torso body 12 are sleeves 32, 34 which can be made of fabric similar to that comprising the torso body. Each sleeve has a length greater than the length of the wearer's arms, and the distal ends 46, 48 of each sleeve include a fastening device 50 adapted to fasten the sleeve ends to one another. In accordance with the invention, the sleeves can be fastened to a belt strap 62 or to some other portion of the strait jacket so as to prohibit the strait jacket wearer from making uncontrolled movements of his or her arms. In the illustrated embodiment, this fastening device 50 comprises a belt and belt buckle, but other known fastening devices such as ropes can be used.

In accordance with yet another aspect of the invention, the sleeves can each have a length permitting the sleeves to be crossed at the center front of the wearer's body as suggested in FIG. 1, and then extended around the back of the wearer's body where they are fastened to the other sleeve at a rear or posterior position. Thus, depending on the length of the sleeves, this sleeve interconnection can be located at the back or at the front of the wearer.

The jacket includes a high annular collar 56, around which, if desired, can be provided as an outer collar 58. These collars 56 and 58 can be made as an integral piece, and can be made integral with the jacket torso body 12, if desired.

To provide additional security, a chest strap 60 extends downwardly from the collar 58 across the wearer's anterior torso and, if desired, under the wearer's crotch. In accordance with one aspect of the invention, the chest strap 60 can be attached to the belt strap 62 adapted to be secured about the wearer's torso and further adapted to be attached to the chest strap at a posterior position. The chest strap 60 can also be attached to the belt strap 62 at an anterior position for additional security and effectiveness.

The following is claimed as invention:

1. A strait jacket adapted to fit wearers of more than one clothing size, the strait jacket comprising, in combination:
   a jacket torso body comprising at least two panels adapted to be located at the back of the wearer, each panel terminating at a lower edge located adjacent to but below the wearer's under arms and above the wearer's waist;
   sleeves each extending from the torso body to a distal end, each sleeve having a length greater than the length of the wearer's arms, the distal end of each sleeve including a fastening device, the sleeves and fastening devices extending sufficiently that the respective fastener devices can be connected to each other behind the wearer's back;
   an annular jacket collar affixed to the jacket torso body;
   a chest strap adapted to extend downwardly from the collar over the torso front; and
   a belt strap adapted to be secured about the wearer's mid rib cage and further adapted to be attached to the chest strap at the torso front.

2. A strait jacket according to claim 1 wherein said torso body panels have edges defining a strait jacket torso body rear opening;
   at least one strap means extending between the back panels; and
   means for connecting each means to the other strap means.

3. A strait jacket according to claim 2 wherein said sleeves each have a length permitting the sleeves to be crossed at the center front of the wearer's body, around the back of the wearer's body, and fastened to the other sleeve at said position behind the wearer's back.

4. A strait jacket according to claim 1 wherein said belt strap is adapted to be attached to said chest strap at an anterior position.

5. A strait Jacket according to claim 1 wherein said jacket torso body has at least one lower edge located above the normal location of the wearer's elbows and below the wearer's shoulders.

6. A strait jacket according to claim 1 wherein said torso panels terminate at lower edge is located below the wearer's under arms and above the wearer's waist.

7. A strait jacket according to claim 1 wherein said strait jacket covers only the wearer's upper back, upper chest, lower neck and arms.

8. A strait jacket according to claim 1 wherein the jacket has a closed front.

* * * * *